United States Patent [19]
Iwabuchi et al.

[11] Patent Number: 5,866,782
[45] Date of Patent: Feb. 2, 1999

[54] GENE WHICH DETERMINES CYTOPLASMIC STERILITY AND A METHOD OF PRODUCING HYBRID PLANTS USING SAID GENE

[75] Inventors: Mari Iwabuchi, Yamato; Takako Sakai, Machida; Hong Jun Liu, Yokohama; Jun Imamura, Machida, all of Japan

[73] Assignees: Mitsubishi Corporation; Mitsubishi Chemical Corporation, both of Tokyo, Japan

[21] Appl. No.: 454,115

[22] PCT Filed: Sep. 30, 1994

[86] PCT No.: PCT/JP94/01625

§ 371 Date: Jul. 12, 1995

§ 102(e) Date: Jul. 12, 1995

[87] PCT Pub. No.: WO95/09910

PCT Pub. Date: Apr. 13, 1995

[30] Foreign Application Priority Data

Oct. 1, 1993 [JP] Japan .................................... 5-269660

[51] Int. Cl.[6] .............................. A01H 5/00; A01H 1/02; C12N 15/29; C12N 15/82
[52] U.S. Cl. .................................. 800/205; 800/DIG. 15; 800/DIG. 17; 536/23.6; 435/172.3; 47/58; 47/DIG. 1
[58] Field of Search .......................... 536/23.6; 800/205, 800/220, DIG. 15, 17; 435/172.3; 47/58, DIG. 1

[56] References Cited

FOREIGN PATENT DOCUMENTS

90/13654  11/1990  WIPO .

OTHER PUBLICATIONS

Patent Abstracts of Japan, vol. 013, No. 532 (C–659), Nov. 28, 1989 & JP–A–01 218530 (Mitsubishi Kasei Corp; others: 01), Aug. 31, 1989, *abstract*.

Sakai et al., "Intergeneric transfer of cytoplasmic male sterility between *Raphanus sativus* (cms line) and *Brassica napus* through cytoplast–protoplast fusion", Theoretical and Applied Genetics, vol. 80, No. 3, pp. 421–427, 1990.

Sakai et al., "Alteration of mitochondrial genomes containing AtpA genes in the sexual progeny of cybrids between *Raphanus sativus* cms line and *Brassica napus* cv. Westar ", Theoretical and Applied Genetics, vol. 84, No. 7–8, pp. 923–929, 1992.

*Primary Examiner*—David T. Fox
*Attorney, Agent, or Firm*—Wenderoth, Lind & Ponack, L.L.P.

[57] ABSTRACT

A novel gene that can be used to identify male-sterile cytoplasm in plants, for example, of the Cruciferae family, and a method for producing hybrid plants using this gene are provided. This novel cms cytoplasmic gene is valuable in that it can be utilized in the production of hybrid plant seeds. This invention is also useful for rapidly identifying Kosena cms cytoplasm, a novel cytoplasm which exhibits characteristics valuable in plant breeding. In addition, this gene may possibly be used to confer cms onto a broad range of plant species, not limited to those of the Cruciferae family, by its introduction into nuclear or mitochondrial genomes.

11 Claims, 10 Drawing Sheets

GENE WHICH DETERMINES CYTOPLASMIC STERILITY AND A METHOD OF PRODUCING HYBRID PLANTS USING SAID GENE

BACKGROUND OF THE INVENTION

1. Field of the Invention

The present invention relates to a gene which determines cytoplasmic sterility in plants, such as of the Cruciferae family, as well as a method for producing hybrid plants by utilization of this gene. Specifically, the present invention relates to a gene for cytoplasmic male sterility and a method for producing hybrid plants by utilizing this gene for the purpose of developing new $F_1$ plant varieties.

2. Description of the Related Art

First filial generations are utilized for many major crop and vegetable plants. First filial generations are characterized by; 1) superior agricultural characteristics resulting from hybrid vigor, 2) homogeneity of harvested products, 3) segregation of genetic characteristics in the subsequent generations, thus protecting the profits of the breeder.

In the Cruciferae family, self-incompatibility is widely used for harvesting $F_1$ seeds. However, in rapeseed, which does not have a stable self-incompatibility system, there is a demand for systems to generate $F_1$ seeds using cytoplasmic male sterility instead (hereafter abbreviated as "cms"). At present, techniques for generating $F_1$ seeds possessing polima cms are being applied. However, because its male sterility characteristic is unstable and flower morphology is poor, which affect the yield of harvest, there is a need for improvement.

Recently, attempts have been made to use Ogura cms derived from Japanese radish in rapeseed in place of polima cms. Male sterility in Ogura cms is stable, and fertility can be restored by a single fertility-restoring gene (hereafter abbreviated as "Rf gene"). The Rf gene of Ogura radish has already been introduced from Japanese radish into rapeseed and it has been ascertained that both the cms and Rf genes of Ogura radish introduced in rapeseed can be put into practical use without problems.

However, cms cytoplasm not only causes pollen sterility, it may also affect other characters of plants. Formerly, one type of maize cytoplasm, T-cms, had been widely used in the generation of $F_1$ seeds, but it conferred susceptibility to two major plant diseases, sesame leaf bright and yellow leaf bright diseases, as well as susceptibility to damage by *Ostrinia nubilalis*. In the 1970's, the first filial corn suffered a severe damage due to major outbreaks of sesame leaf bright. Since then it has been recognized that the use of only a single type of cytoplasm for the production of $F_1$ seeds is very dangerous.

In addition, cms cytoplasm may influence flower morphology. For example, in the case of rapeseed carrying polima cms cytoplasm it is known that large openings may form in the base of the petal through which bees are able to obtain nectar. This circumvents the normal process of pollen transfer, ultimately leading to problems in the yield of seed in polima cms plants. In addition, flower size in Japanese radish carrying Ogura cms cytoplasm is smaller than that in fertile individuals and the volume of secreted nectar is low, which results in infrequent visits by pollinating insects. Thus, Japanese radish carrying Ogura cms cytoplasm also exhibit problems in seed yield. When Japanese radish carrying cms cytoplasm derived from Kosena radish ("Kosena") was tested, it was found that the seed yield was higher than that in plants in which Ogura cms cytoplasm had been used. This suggests that the cms cytoplasm from Kosena is genetically different from that of Ogura. That is, this phenotypic difference appears to be caused by the result of the interaction between cytoplasmic genetic factors, viz. mitochondria and chloroplasts, and nuclear genes. It was thought that by introducing this cytoplasm by crossing or cell fusion into useful crops other than Japanese radish there would be a high probability of obtaining varieties with superior morphological characteristics.

In addition, the negative effects resulting from incompatibility between the nucleus and cytoplasm, which occurs when cms cytoplasm is introduced into heterologous plant species, can be removed to some degree by cell fusion. The cytoplasmic genomes (chloroplasts and mitochondria) in cytoplasmic hybrid plants (cybrids) formed by cell fusion often consist of recombinants derived from both parental genomes. Using this phenomenon, we could select cybrids into which only the cms gene has been introduced. In this process, It was thought that the introduction of cms cytoplasm which does not cause problems with respect to petal or nectar yield would increase chances of obtaining cybrids advantageous for plant breeding.

SUMMARY OF THE INVENTION

Japanese radish cytoplasm introduced into rapeseed is only Ogura cms cytoplasm thus far. However, considering the earlier problems encountered with corn, it is desirable that cytoplasms genetically different from Ogura cms be used concurrently in plant breeding.

The present inventors, as a result of a search for cytoplasm genetically different from Ogura cms, found that cms derived from Kosena radish is extremely useful in the development of $F_1$ plant varieties. By obtaining the gene responsible therefor, the present invention was achieved.

In summary, the purpose of the present invention is to provide the gene encoding the polypeptide whose amino acid sequence is shown in Sequence ID No:1 in the Sequence Listing, and to provide a method for preparing hybrid plants using such gene.

BRIEF DESCRIPTION OF THE DRAWINGS

FIG. 5 is a diagram showing the physical map of a mitochondrial DNA region which contains orf125 or orf138. In the figure, "Ogura" indicates an approximate 2.5 kb NcoI DNA fragment from Ogura radish cms-type mitochondria, "Kosena" indicates an approximate 2.5 kb NcoI DNA fragment from Kosena radish cms-type mitochondria, and "CMS cybrid" indicates an approximate 3.2 kb DNA fragment containing orf125 from cms-rapeseed mitochondria. "125", "138" and "B" refer to orf125, orf138 and orfB, respectively, and "Nc", "Hc" and "Xb" indicate the cleavage sites by the NcoI, HincII and XbaI restriction enzymes, respectively. The arrow indicates the differences in the orf125 regions between cms-rapeseed and Kosena radish. Thus, the sequences lying downstream of 34th base from the stop codon of orf125, which is indicated by the arrow, differ between these two species.

FIGS. 10A–10B show the construction of the binary vector used for transformation. Section (A) shows the binary vector pKM424. pKCM125 and pKCMD125 were constructed by insertion of the promoter sequence, gene and terminator sequence shown in B into the HindIII (H) and EcoRI (E)-digested multicloning site (MCS) of pKM424. "35S" shown in the figure indicates the cauliflower mosaic virus 35S promoter sequence, "125" indicates the orf125 gene, "D" indicates the mitochondrial targetting sequence, "NOS" and "NOST" indicate the terminator sequence from the nopaline synthase gene, "RB" indicates the right border sequence, "NPTII" indicates the Neomycin phosphotransferase gene, "NOSP" indicates the promoter sequence of nopaline synthase gene promoter, "SpecR" indicates the Spectinomycin resistance gene, and "TcR" indicates the Tetracycline resistance gene.

DETAILED DESCRIPTION OF THE INVENTION

The present invention is described in detail below.

First, the genetic characteristics of the cms cytoplasm and Rf gene within the Kosena radish population (*Raphanus sativus,* cv. Kosena) were examined by crossing. For example, the inventors randomly chose a male-sterile (cms) plant of Kosena radish (*R. sativus,* CMS line) and crossed it using pollen obtained from fertile Kosena radish or radish cultivars, for example "Yuanhong" (*R. sativus,* cv. Yuanhong). Individuals in the subsequent generation obtained by crossing fertile and sterile individuals were then examined for fertility. Because the inventors observed some plants crossing with male-sterile Kosena that gave rise to all fertile individuals in the subsequent generation, they assumed that the pollen donor was of the Rf line and carried the Rf gene in the homo configuration.

Next, the inventors randomly chose several male-sterile individuals from the Kosena population. These individuals were pollinated by the several pollen donors which had been determined in the above experiment to be of the Rf line, and fertility in the next generation was examined. From this, the specific interaction between the cms cytoplasm and the Rf gene was elucidated.

Subsequently, the Kosena cms was introduced by, e.g. cell fusion (Japanese Patent Publication (Kokai) No. 218530/1989), into plants carrying an Rf gene with which it had been shown it could specifically interact.

Next, the inventors selected plants which had been converted to cms following the cell-fusion-mediated introduction of part of the Kosena mitochondria, and by conducting crossing experiments as well as analysis of chromosome number, they were able to obtain plants in which fertility was restored by a single nuclear gene.

Next, the inventors isolated a gene which determined CMS cytoplasm in Kosena radish. Specifically, they isolated mitochondria from seedlings of Kosena radish carrying cms cytoplasm (*R. sativus,* CMS line) by standard methods, and they extracted DNA by standard methods from the isolated mitochondria. This mitochondrial DNA was digested with appropriate restriction enzymes, ligated into a cloning vector such as pUC19, and the vector was introduced into *E. coli* competent cells. The *E. coli* colonies were transferred to nylon membranes, etc. and subjected to colony hybridization analysis using a probe prepared from a fragment of the gene isolated from Ogura cms cytoplasm (International Patent Publication No. WO 92/05251). Plasmids DNA were extracted from the positive colonies by standard methods and the nucleotide sequence of the recovered DNA was determined by e.g. dideoxy sequencing method of Sanger et al. One example of the nucleotide sequence of the DNA fragments thus obtained is the one encoding the polypeptide whose amino acid sequence is shown in Sequence ID No:1 in the Sequence Listing, or preferably, is the nucleotide sequence shown in the same Sequence ID No:1. The DNA fragment obtained is derived from Kosena radish, and its sequence may be altered by e.g. deletion, insertion, modification or addition of nucleotides to the extent that such alteration does not impair fertility restoration of plants carrying it, particularly of the Cruciferae.

Furthermore, in order to be able to identify cms mitochondria that can revert CMS plants to a fertile state by the single nuclear gene as described above, a specific gene was found within the mitochondrial genome. With this gene, it is possible to develop methods by which the cytoplasms can be easily identified.

According to the present invention, the gene obtained as described above may be introduced into the nuclear genome by conventional methods, or introduced directly into the mitochondrial genome to generate a recombinant mitochondrial genome. Furthermore, transgenic plants or cybrid plants possessing male sterile cytoplasm containing said mitochondrial genome may be used in the production of hybrid plants. For example, in the case of rapeseed, methods for regeneration following the introduction of DNA by the transformation technique utilizing Agrobacterium (Japanese Patent Publication (Kohyo) No. 500718/1989) are known, as well as cybrid techniques for cell culture and plant regeneration following the introduction of DNA into protoplasts by electroporation (Plant Science 52, 111–116, 1987).

Plants utilized for transformation include members of the Cruciferae, the Solanacae, etc., and more preferably rapeseed and tobacco, etc. Of these rapeseed is the plant most preferred.

Hybrid plants may be obtained by, for example, the method described in European Patent Publication (laid-open) No. 599042 using the above-mentioned transformed plants or cybrids as the pollen recipients. As pollen donors, plants are used into which a fertility-restoring gene with the ability to restore fertility of the recipient plants carrying the cms cytoplasm has been introduced. Thus, fertilization of the recipient plants restores their ability to produce fertile pollen. The hybrids are prepared by conventional crossing techniques.

The present invention is illustrated in a more specific manner by the following examples. It is understood that the invention is not limited to these embodiments insofar as the application does not exceed the essential point of the invention.

Example 1: Genetic Analysis of the Kosena Radish cms

Ten individual cms-Kosena radish plants (R. sativus, cv. Kosena CMS line; KosA) were randomly chosen and pollinated by fertile Kosena radish (R. sativus, cv. Kosena), or the cultivated varieties of Japanese radish, Yuanhong (R. sativus, cv. Yuanhong) or Xinlimei (R. sativus, cv. Xinlimei). Seeds were also obtained from the 16 pollen donors by self-pollination. Sixteen pairs of cms-Kosena radish and fertile Japanese radish were crossed and next the fertility of 9 to 25 individual progeny from each crossing was examined. These results are shown in Table 1. From these, pollen donors which produced all fertile progeny, namely Kos 6, Kos 8, Xin 1, Xin 2, Xin 4, Xin 8, Yuan 1, Yuan 6, Yuan 7, Yuan 8, Yuan 10, and Yuan 13, were designated as of the Rf line and assumed to carry the homozygous Rf genes.

TABLE 1

Genetic pattern of the fertility-restoring gene effective against Kosena radish male sterility

| Crossed pair | | | Fertility of $F_1$ generation | | Genotype of the fertile parent |
|---|---|---|---|---|---|
| sterile[1] | x | fertile[2] | sterile | fertile | (inferred) |
| KosA2 | x | Kos1 | 7 | 15 | Rfrf |
| KosA11 | x | Kos5 | 25 | 0 | rfrf |
| KosA11 | x | Kos6 | 0 | 22 | RfRf |
| KosA8 | x | Kos7 | 6 | 3 | Rfrf |

TABLE 1-continued

Genetic pattern of the fertility-restoring gene effective against Kosena radish male sterility

| Crossed pair | | | Fertility of $F_1$ generation | | Genotype of the fertile parent |
|---|---|---|---|---|---|
| sterile[1] | x | fertile[2] | sterile | fertile | (inferred) |
| KosA8 | x | Kos8 | 0 | 18 | RfRf |
| KosA2 | x | Xin1 | 0 | 25 | RfRf |
| KosA1 | x | Xin2 | 0 | 25 | RfRf |
| KosA7 | x | Xin4 | 0 | 25 | RfRf |
| KosA11 | x | Xin8 | 0 | 25 | RfRf |
| KosA2 | x | Yuan1 | 0 | 25 | RfRf |
| KosA5 | x | Yuan6 | 0 | 25 | RfRf |
| KosA1 | x | Yuan7 | 0 | 25 | RfRf |
| KosA12 | x | Yuan8 | 0 | 25 | RfRf |
| KosA13 | x | Yuan9 | 11 | 14 | RfRf |
| KosA14 | x | Yuan10 | 0 | 25 | RfRf |
| KosA15 | x | Yuan13 | 0 | 25 | RfRf |

[1]KosA: a cms line of Kosena radish (R. sativus, cv. Kosena).
[2]Lines which carry fertility-restoring gene effective against Kosena cms cytoplasm. Kos: Kosena radish (R. sativus, cv. Kosena), Xin: Xinlimei (R. sativus, cv. Xinlimei), Yuan: Yuanhong (R. sativus, cv. Yuanhong).

Next, the inventors randomly chose individual cms-Kosena plants, crossed them with plants of the Kos 6 and Yuan 10 lines, shown to be of the Rf line by the experiment described above, and examined the fertility of these progeny. The results showed that some Kosena plants give rise to fertile progeny only when crossed with Yuan 10 (cms-KAC), whereas others give rise to fertile progeny when crossed with either Kos 6 or Yuan 10 (cms-KA).

Next, Kos 6 and Yuan 10 were crossed with a sterile line of Ogura radish (R. sativus, cv. Ogura CMS line). The experimental results showed that all progeny of the Ogura× Yuan 10 were fertile, whereas all of the progeny of the Ogura×Kos 6 were male-sterile. Thus, while Kos 6 is of a line which restores fertility of the plants carrying cms-KA, it does not carry an Rf gene effective against Ogura cms. These results revealed that the Kosena cms cytoplasm is genetically distinct from the former Ogura cytoplasm (hereafter designated "cms-OGU"). The above results are summarized in Table 2.

TABLE 2

Analysis of Kosena cytoplasmic male sterile cytoplasms exhibiting genetically-distinct modes of restoration by the restorer genes

| Crossed pair | | | Segregation of fertility in $F_1$ generation | | Genotype of fertile individuals |
|---|---|---|---|---|---|
| sterile | x | fertile | fertile | sterile | (inferred) |
| cms-KAC | x | Yuan10 | 10 | 0 | Rf1Rf2 |
| cms-KA | x | Yuan10 | 5 | 0 | Rf1Rf2 |
| cms-OGU | x | Yuan10 | 10 | 0 | Rf1Rf2 |
| cms-KAC | x | Kos6 | 0 | 8 | rf1Rf2 |
| cms-KA | x | Kos6 | 25 | 0 | rf1Rf2 |
| cms-OGU | x | Kos6 | 0 | 15 | rf1Rf2 |

Figure 1:
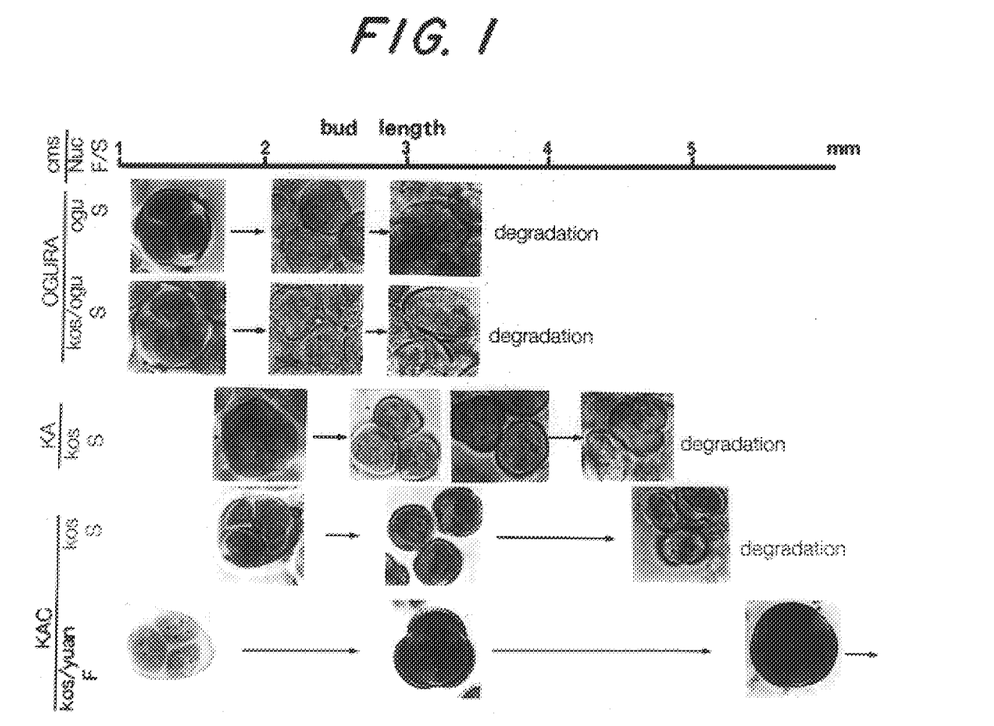
FIG. 1 represents photographs displaying the development of pollen in cms-KA, cms-KAC and cms-OGU, wherein "KAC" indicates cms-KAC, "KA" indicates cms-KA, "OGURA" indicates cms-OGU.

The cms-KA and cms-KAC also exhibit differences from cms-OGU in the stage of pollen degradation (FIG. 1). FIG. 1 shows the length of flower bud and pollen developmental stage visualized by the acetocarmine staining of Japanese radishes carrying various types of cytoplasms. The pollen degradation stage and extent of development varies with the cytoplasm and the nuclear background. "cms" indicates cytoplasm, "Nuc" indicates the genomic composition, as shown in Table 3 below.

TABLE 3

| Cytoplasm | Nucleus designation | Nuclear genome |
|---|---|---|
| cms-KAC | kos/yuan | kosena 6 × yuanhong 10 |
|  | kos | kosena 6 |
| cms-KA | kos | kosena 5 |
| cms-OGU | kos/ogu | kosena 6 × ogura 3 |
|  | ogu | ogura 3 |

The numbers shown beside the nuclear genome designations refer to the number of the individual chosen within the original population (refer to Table 1).

In the case of cms-OGU plants it was observed that pollen degradation had already commenced at the point where the bud length had reached 3 mm. In comparison pollen degradation in cms-KA and cms-KAC plants occurred at the point where bud length had reached 4.5 mm. This difference was independent of the composition of the nuclear genome, suggesting that this difference was caused by cytoplasmic rather than nuclear factors.

Example 2: Examination of the Ability of cms Cytoplasm to be Restored by a Single Gene Previously the Kosena radish cms had been introduced into rapeseed (*B. napus*) by cell fusion (Japanese Patent Publications (Kokai) No.218530/1989, 303426/1990). Fertility of this cms rapeseed could not be restored by a gene from its own species but could be restored by crossing with Japanese radish carrying an Rf gene. However, the number and inheritance of the Rf gene thus introduced was not examined. It was therefore investigated whether this rapeseed was carrying the cms cytoplasm capable of being restored by a single Rf gene. This was accomplished using rapeseed that had contained both Kosena and rapeseed mitochondrial genomes as a result of cell fusion (hereafter referred to as "cms-rapeseed").

cms-rapeseed was crossed with plants of the Kosena Rf line-Yuan 10 line, and of the resulting double haploid plants an individual that had restored was selected (hereafter referred to as "cms/Rf-rapeseed"). This individual was back-crossed twice with Westar (*B. napus*, cv. Westar), a fertile variety that does not carry cms cytoplasm. Subsequently an individual exhibiting good fertility was chosen and it was crossed with cms-rapeseed (Japanese Patent Publication (Kokai) No. 141715/1994). These results are shown in Table 4.

TABLE 4

Genetic analysis of Kosena-derived fertility-restoring gene using cms-rapeseed

| cms-rapeseed | x | Restorer line | Fertility of $F_1$ generation fertile:sterile |
|---|---|---|---|
| SW18 | x | RF138 | 84:89 |
| SW18 | x | RF88 | 80:71 |

Sterile and fertile individuals emerged in the subsequent generation in an approximate 1:1 ratio. Furthermore, by acetocarmine staining of the cms/Rf-rapeseed chromosomes it was found that the chromosome number of the line obtained after the 2 back-crossing equalled 38, the same number as the starting rapeseed plant. From this it was recognized that the Rf gene of cms/Rf-rapeseed had been incorporated into the rapeseed genome by translocation. It was thought that the possibility of multiple Rf genes translocating to the same chromosome would be extremely low. Thus, it was concluded that the cms-rapeseed carrying this cytoplasm could be restored by the action of a single gene and would be excellent for use in plant breeding.

Example 3: Identification of cms Cytoplasm Using a Mitochondrial Gene

Previously, a gene specific to Ogura cms cytoplasm had been isolated (hereafter referred to as "orf138") (International Patent Publication No. WO 92/05251). A homologous gene was isolated from Kosena radish.

(1) Extraction of Mitochondrial DNA

Five grams of seeds from Kosena radish carrying cms cytoplasm (*R. sativus*, CMS line) were allowed to sprout in the dark. Five-day-old seedlings were homogenized with a chilled mortar and pestle in a buffer for mitochondria extraction [2 ml per 1 g. of tissue: 0.4M Sorbitol, 1mM EDTA, 0.1% BSA, 0.1M Tris-HCl (pH 8.0)] and an appropriate amount of sea sand C. The homogenate was centrifuged at 200×g, at 4° C. for 5 min. and the supernatant was transferred to a new centrifuge tube. The tube was centrifuged at 1,500×g, at 4° C. for 5 min., and the supernatant was transferred to a new centrifuge tube. This procedure was repeated twice. Next, the sample was centrifuged at 15,000× g, at 4° C. for 5 min. to pellet the mitochondria. This pellet was gently resuspended in 2 ml. of a buffer [0.3M sucrose, 50 mM Tris-HCl (pH 7.5), 10 mM $MgCl_2$] containing 100 g deoxyribonuclease per 1 g tissue and allowed to stand at 4° C. for 30 min. This mitochondrial suspension was layered on top of 15 mls of Shelf buffer [0.6M sucrose, 20 mM EDTA, 10 mM Tris-HCl (pH7.2)] and centrifuged at 15,000×g, at 4° C. for 5 min. The pelleted mitochondria was gently re-suspended in 15 ml. of Shelf buffer and re-centrifuged at 15,000×g for 5 min. at 4° C. To the pelleted mitochondria was added 1.5 ml. of a buffer for DNA extraction [1% N-laurylsarkosine, 20 mM EDTA, 50 mM Tris-HCl(pH8.0)]. After the pellet had been dissolved, 1.5g of CsCl was added and dissolved. Ethidium bromide solution was added to a final concentration of 200 μg/ml and the mixture was centrifuged at 350,000×g for 14 hrs. The fraction containing mitochondrial DNA was collected, extracted by n-butanol to remove the ethidium bromide, and the CsCl was removed by dialysis against a buffer composed of 10 mM Tris-HCl, 1 mM EDTA (pH8.0).

(2) Isolation of DNA Specific to Kosena cms Mitochondria

Mitochondrial DNA was digested with NcoI, blunt-ended, and ligated into the SmaI site of the plasmid vector pUC19. The recombinant plasmids was introduced into competent DH5α *E. coli* cell, and cultured on LB agar plates containing 50 μg/ml of ampicillin. The *E. coli* colonies which grew up were transferred to nylon membranes and sequentially placed on filters soaked with solutions as follows: 10% SDS for 5 min. to lyse bacteria, an alkaline solution [1.5M NaCl, 0.5M NaOH] to denature DNA, and a neutralization solution [3M sodium acetate, pH5.2]. The membranes were subsequently dried at 80° C. for 10 min. and soaked in 6×SSC [1×SSC: 150 mM NaCl, 15 mM sodium citrate] for 30 min. Debris was removed from the membrane surfaces by wiping with a JK wiper containing 6×SSC and then washed by shaking in 6×SSC, after which the membranes were thoroughly dried at 80° C. Next, a HincII fragment of approximately 0.7 kb containing the gene specific to Ogura cms cytoplasm orf138, was labeled by random primer method for use as a hybridization probe. Hybridization was performed at 42° C. for 16hrs. in 5×SSCP [1×SSCP: 50 mM sodium phosphate (pH 6.8), 120 mM NaCl, 15 mM sodium citrate], 50% formamide, 100 µg/ml heat-denatured salmon sperm DNA, 0.5% skim milk, and 0.5% SDS. Next, the membranes were washed by shaking in 2×SSC at 42° C., 3 times for 15 mins. each, after which they were washed in 0.1×SSC at 65° C. for 30 min. Radioactivity remaining on the filters was detected by X-ray film and *E. coli* colonies corresponding to those which gave a strong positive signal were picked, cultured, and their plasmid DNAs were extracted. The plasmid isolated (hereafter referred to as pKOS2.5) contained an approximate 2.5 kb DNA fragment. When pKOS2.5 was digested with the restriction enzyme HincII and subjected to Southern hybridization, it was found that the probe described above hybridized to a band of 0.65 kb. This 0.65 kb DNA fragment was then subcloned into the SmaI site of the plasmid vector Bluescript II (Stratagene). Next the nucleotide sequence of this HincII DNA fragment was determined by dideoxy sequencing and a 659 bp sequence was obtained (Sequence ID No:1 in the Sequence Listing).

Figure 2:
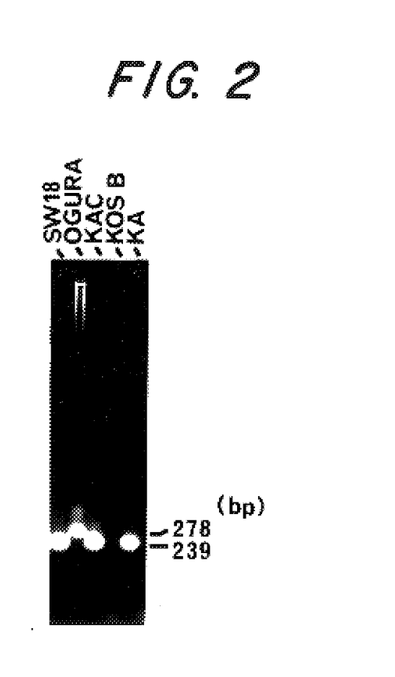
FIG. 2 is a photograph showing the electrophoretic patterns which demonstrates identification of cms cytoplasms using the PCR method. In the figure, "SW18" indicates cms-rapeseed, "OGURA" indicates cms-OGU, "KAC" indicates cms-KAC, "KOS B" indicates the normal form of Kosena radish mitochondria, and "KA" indicates cms-KA.

Within this nucleotide sequence was a gene (hereafter referred to as "orf125") which encodes 125 amino acids. The orf125 contained 39 nucleotides deletion as compared with the nucleotide sequence in orf138. The deleted sequence corresponded to part of a repeated sequence in orf138. Primers were designed which could detect the length of this repeat (shown in Sequence ID No:2 and No:3 in the Sequence Listing), and PCR reaction was conducted using total DNAs from Kosena carrying cms-KA, cms-KAC or normal cytoplasm, cms-rapeseed, and cms-OGU. The PCR reaction was carried out at 94° C. for 25 secs., 52° C. for 30 sec., and 72° C. for 90 secs. for 40 cycles (Am. J. Hum. Genet., 37, 172 (1985)). The gel electrophoretic pattern produced by these PCR products is shown in FIG. 2. A 278 bp band from Ogura-type cms cytoplasm and a 239 bp band from Kosena-type cms cytoplasm were detected. From these results it was determined that orf125 is not present in normal Kosena mitochondria or cms-OGU but is present in cms-KA, cms-KAC and cms-rapeseed. Thus, orf125 was determined to be a gene specific to Kosena cms mitochondria.

(3) Discrimination of cms-KA and cms-KAC

Figure 3:
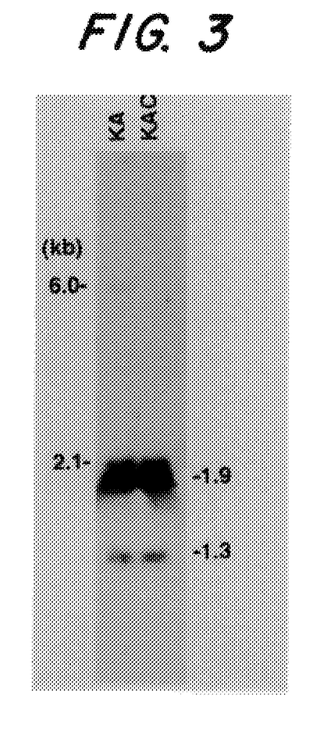
FIG. 3 is a photograph showing the Southern hybridization patterns of mitochondrial DNA derived from cms-KA and cms-KAC using rrn26 as a probe. In the figure, "KA" indicates cms-KA and "KAC" indicates cms-KAC.

Given that cms-KA and cms-KAC are genetically different cms cytoplasms, we assumed that there should be some difference in their mitochondrial genomes. Thus, mitochondrial DNAs were extracted from these two types of cms and attempted to detect any difference by Southern hybridization using several DNA fragments including mitochondrial genes as probes. The DNA fragments used as probes are as follows: atpA (pea), atp9 (pea), atp6 (Oenothera), cob (maize), coxI, rps13 and nad1 (Oenothera), coxII (maize), coxIII (Oenothera), rrn5, rrn18 and nad5 (Oenothera), and rrn26 (pea). Hybridizations were performed under the conditions described previously. A 6.0 kb band specific to cms-KA was detected only when a 0.5 kb EcoRI-SalI DNA fragment containing the pea rrn26 was used as the probe (FIG. 3).

Next, total RNA was extracted from the buds of fertile and sterile individuals from plants carrying cms-KA or cms-KAC-type mitochondria. The RNA was extracted by the following protocol.

Figure 4:
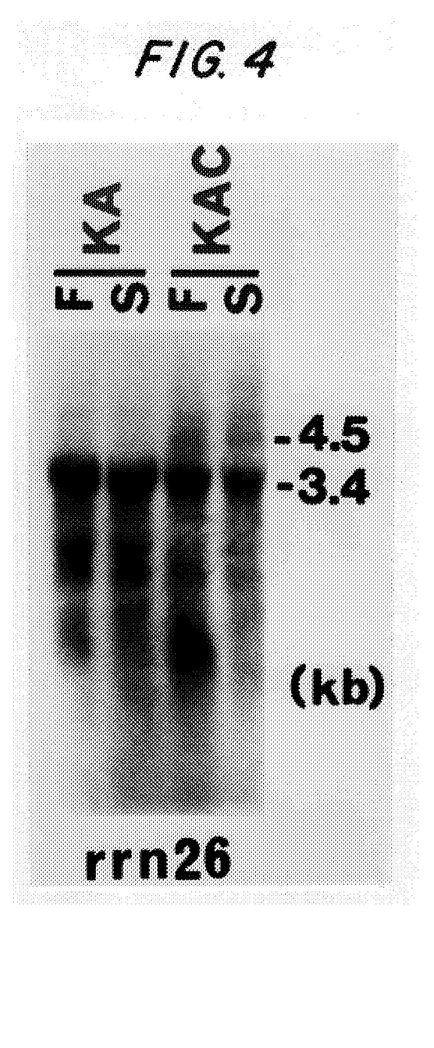
FIG. 4 is a photograph showing the Northern hybridization patterns of cms-KA and cms-KAC using rrn26 as a probe. In the figure, "KA" indicates cms-KA, "KAC" indicates cms-KAC, and "F" and "S" indicate fertile and sterile, respectively.

One gram of buds was homogenized in liquid nitrogen with a mortar and pestle, to which was added 10 mls of RNA extraction buffer [4M guanidine thiocyanate, 25 mM sodium citrate (pH7.0), 0.5% sodium N-lauroylsarcosinate, 0.1M EDTA]. This suspension was transferred to a centrifuge tube, 1 ml of 2M sodium acetate (pH4.6) was added and mixed, and subsequently 10 ml. of water-saturated phenol and 2 ml. of chloroform/isoamyl alcohol (24:1) were added and the suspension was mixed well. The mixture was centrifuged at 1,500×g, for 20 mins. at 4° C., the upper phase was cooled and extracted twice with chloroform/isoamyl alcohol, and RNA was precipitated by the addition of an equal volume of isopropyl alcohol. RNA was collected by centrifugation at 15,000×g, for 10 mins at 4° C. and the precipitate was thoroughly dissolved in 1 ml of RNA extraction buffer. Next, 0.1 ml of 2M sodium acetate (pH4.6), 1 ml of water-saturated phenol and 0.2 mls. of chloroform/isoamyl alcohol were added and the mixture was centrifuged at 7,500×g, at 4° C. for 20 min. The upper phase was extracted twice with chloroform/isoamyl alcohol and the RNA was precipitated by the addition of 2 volumes of ethanol. RNA was collected by centrifugation at 15,000×g, at 4° C. for 10 min. and re-dissolved in sterilized water. Next, 10 µg of RNA was subjected to gel electrophoresis in a denaturing gel containing formaldehyde and subjected to Northern hybridization using rrn26 as a probe. Hybridization was carried out under the conditions described above. The hybridization patterns of plants carrying cms-KA and cms-KAC-type mitochondria were different. A 4.5 kb band was detected in samples from both fertile and sterile cms-KAC, which was not found in the cms-KA samples (FIG. 4). From this result it was determined that cms-KA and cms-KAC differ in the regions of their mitochondria genomes homologous to rrn26 and that these two types of mitochondria could be distinguished using rrn26 as a probe in Southern or Northern hybridization analysis.

Figure 5:
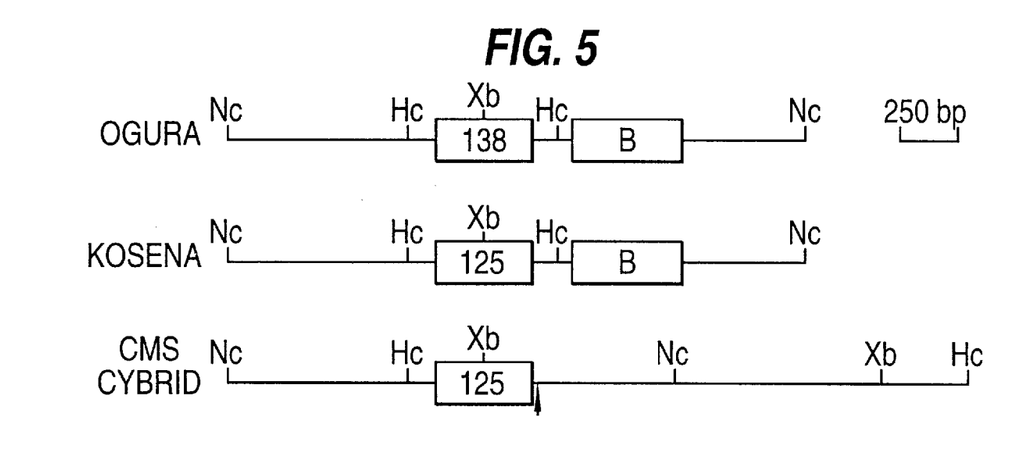

(4) DNA Fragment Used to Identify cms Cytoplasm of cms-rapeseed Restored by a Single Kosena Rf Gene To further identify the cms cytoplasm of cms-rapeseed restored by a single Rf gene of Kosena radish, a mitochondrial region specific to the cms-rapeseed was examined. Mitochondrial DNA was extracted from the cms-rapeseed, digested with NcoI, HincII and XbaI, and using a 0.33 kb HincII-XbaI DNA fragment from the 5' end and a 0.33 kb XbaI-HincII DNA fragment from the 3' end of orf125 as probes, Southern hybridization was performed. From this analysis, it was found that the physical map of a region containing orf125 of cms-rapeseed differs from that of Kosena radish (FIG. 5). Orf138 is present in Ogura cms-type mitochondria and orfB resides immediately downstream. In Kosena radish, orfB resides immediately downstream of orf125 in a 2.5 kb NcoI DNA fragment containing orf125, regardless of whether of the fragment was obtained from cms-KA or cms-KAC type mitochondria (FIG. 5). On the other hand, the region downstream of orf125 in mitochondrial DNA from cms-rapeseed differed from that of Kosena. When mitochondrial DNA of cms Kosena radish was digested with HincII and probed with the 0.33 kb XbaI-HincII fragment containing the 3' region of orf125 in Southern hybridization, a band of 650 bp was detected, whereas in cms-rapeseed mitochondrial DNA, a band of 2.5 kb was detected. The 2.5 kb HincII DNA fragment containing orf125 shown in FIG. 5 is specific to cms-rapeseed mitochondrial DNA, and its presence or absence can thus be used to identify the cms-rapeseed cytoplasm.

(5) Determination of the Nucleotide Sequence of the DNA Fragment Described Above Which can Identify the cms Cytoplasm of Rapeseed Mitochondrial DNA from the cms-rapeseed (SW18 line) was digested with XbaI, ligated into the XbaI site of pBluescript 11 (Stratagene) and the reaction products was used to transform competent DH5α *E. coli*. Colony hybridization was performed using the coding region of orf125 as a probe, and two positive clones were obtained. Plasmid DNAs were extracted from the clones and a physical map was prepared by restriction nuclease digestions. These two clones pSWX2.8 and pSWX1.7 were found to contain the 5' region and 3' region, respectively, of orf125.

Next, pSWX1.7 was digested with the restriction enzyme EcoRV and subcloned into pBluescript 11 (Stratagene) to obtain a clone pSWV0.7, containing orf125, and pSWV0.2, containing sequences downstream of orf125. The nucleotide sequences of these clones, as well as of the HincII-XbaI fragment of pSWX2.8 containing N-terminal region of the orf125, were determined by the dideoxy sequencing method (Sequence ID No:4 in the Sequence Listing). It was found that the region downstream of 34th base of the orf125 stop codon was completely different between SW18, the cms-rapeseed line, and Kosena radish, and that orfB was lacking in the former. The orf125 region of cms-rapeseed described above is hereafter referred to as "orf125c".

Figure 6A:
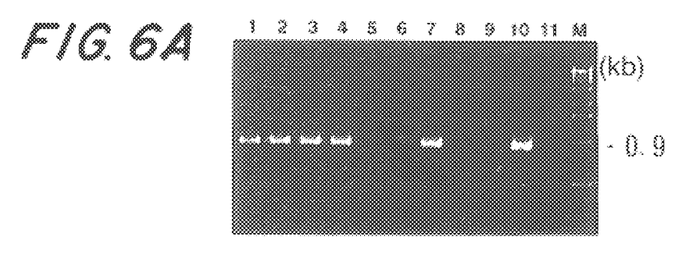
FIGS. 6A–6B consist of photographs showing the electrophoretic patterns of mitochondria genomes identified by the PCR method. "A" indicates PCR analysis using primers of the sequences shown in Sequence ID No:3 and No:6 in the Sequence Listing, "B" indicates PCR analysis using primers of the sequences shown in Sequence ID No:3 and No:5 in the Sequence Listing. In the figure, "1" indicates the cms-KA (fertile) sample, "2" indicates cms-KA (sterile), "3" indicates cms-KAC (fertile), "4" indicates cms-KAC (sterile), "5" indicates normal mitochondria of Kosena radish, "6" indicates SW18, "7" indicates SW12, "8" indicates FW18, "9" indicates normal mitochondria of rapeseed, "10" indicates pKOS2.5, "11" indicates pSW18X1.7, and "M" indicates the size markers.
Figure 6B:
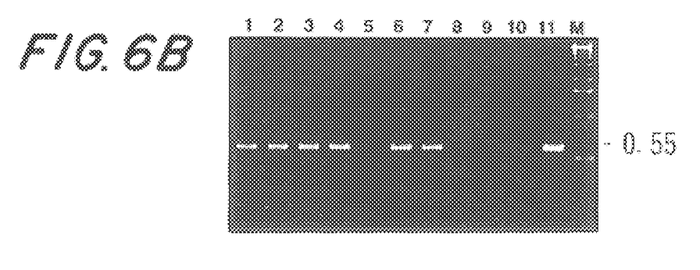

Next, the PCR was conducted to examine whether cms-rapeseed mitochondrial DNA contained the orf125 region found in cms-Kosena radish in addition to orf125c (FIG. 5). Two sets of PCR primers were used for this analysis. One set contained sequences from the coding region of orf125: 5'-GACATCTAGAGAAGTTAAAAAAT-3' (Sequence ID No:3 in the Sequence Listing), and from the region downstream of the orf125c coding region from pSWV0.7: 5'-TCTGACAGCTTACGATG-3' (Sequence ID No:5 in the Sequence Listing). The other set consisted of a combination of Sequence ID No:3 from the Sequence Listing as shown above and a nucleotide sequence found downstream of orfB in pKOS2.5: 5'-CTACCAGAGGTATCTATAGAAT-3' (Sequence ID No:6 in the Sequence Listing). A 0.55 kb band was detected in the cms-rapeseed line plant, SW18, using the former primer set, but no band was detected with the latter primer set (FIG. 6, lane 6). In the cms-Kosena radish and the cms-rapeseed line, SW12, a 0.55 kb band was detected using the former primer set, as had been seen in SW18, and a 0.9 kb band was detected using the latter primer set (FIG. 6, lanes 1–4 and 7). From the results, it was confirmed that orf125c carried by the cms-rapeseed line plant SW18 is derived from the cms mitochondria of Kosena radish. Thus, it was determined that orf125c had been selectively incorporated into the mitochondria genome of the cms-rapeseed line SW18 at the time of cell fusion with Kosena radish. These showed that it is easily conducted to distinguish it from the cms mitochondrial genome of Kosena radish by the PCR method.

(6) Correlation Between orf125 and Male-sterility

Figure 8:
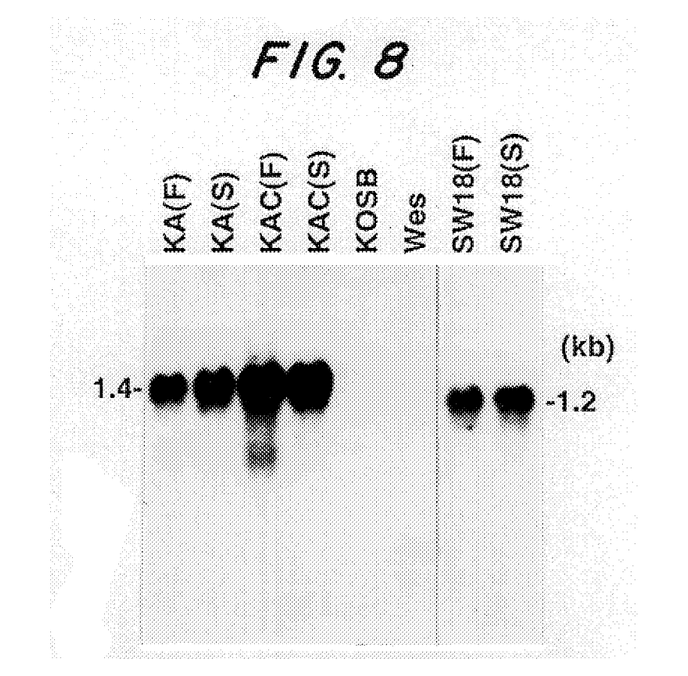
FIG. 8 is a photograph showing the Northern hybridization probed with orf125 after electrophoresis. In the figure, "KOSB" indicates Kosena radish carrying normal mitochondria, "KA" indicates cms-KA, "KAC" indicates cms-KAC, "SW18" indicates cms-rapeseed, "Wes" indicates rapeseed carrying normal mitochondria, and "F" and "S" indicate fertile and sterile, respectively.

Total mitochondrial RNA was extracted from flower buds of cms-Kosena radish and cms-rapeseed by the methods described above, Northern hybridization was performed by the methods described above using the orf125 coding region as a probe. A 1.4 kb band was detected in cms-Kosena radish and a 1.2 kb band was detected in cms-rapeseed (FIG. 8), indicating that the orf125c is transcribed in the cms-rapeseed mitochondria.

Figure 7:
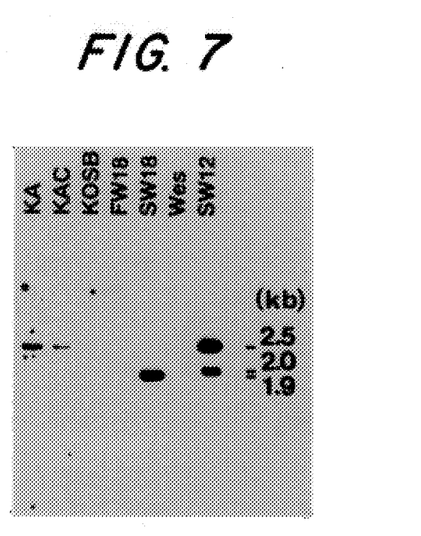
FIG. 7 is a photograph showing the Southern hybridization probed with orf125 after electrophoresis of mitochondrial DNAs digested with the restriction enzyme NcoI. In the figure, "KOSB" indicates Kosena radish carrying normal mitochondria, "KA" indicates cms-KA, "KAC" indicates cms-KAC, "SW18" indicates cms-rapeseed, "FW18" indicates the fertile restorer of rapeseed line, "SW12" indicates cms-rapeseed, and "Wes" indicates rapeseed carrying normal mitochondria.

The cms-rapeseed line SW18 was pollinated by rapeseed carrying normal cytoplasm and no Rf gene, and it was found that among plants in the succeeding generation an individual which showed complete reversion to the fertile state existed. Subsequent generations produced by self-pollination of this individual were all fertile. This rapeseed was designated a fertile revertant line, FW18. It was examined whether orf125 was present in the mitochondrial genome of the FW18 line by PCR and Southern hybridization, but no evidence of existence of orf125 was found by either method (FIG. 6, lane 8, FIG. 7). From the above results, orf125 was found to be a gene responsible for CMS.

(7) Transformation of Plants with the orf125 Gene

Figure 9:
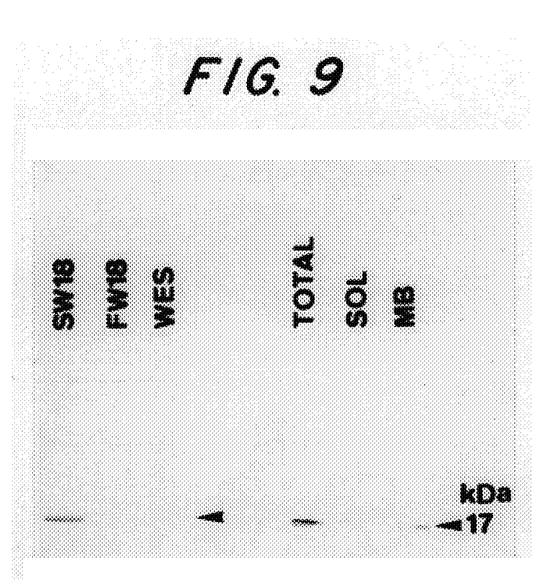
FIG. 9 is a photograph showing the results of Western analysis of mitochondrial proteins performed using an antibody against orf125. Section A shows the analysis of total mitochondrial proteins. In this figure, "SW18" indicates cms-rapeseed, "Wes" indicates fertile rapeseed carrying normal mitochondria, "FW18" indicates a fertile restorer of rapeseed line. Section B shows the analysis of cms rapeseed mitochondrial proteins. In this figure, "TOTAL" indicates total mitochondria, "SOL" indicates the soluble protein fraction and "MB" indicates the membrane-bound protein fraction.

Mitochondria was isolated from 5 days-old seedlings grown in the dark and 10 μg of total mitochondrial proteins were fractionated on a 12% SDS-polyacrylamide gel. Western analysis was performed using an antibody against a 15-amino acid polypeptide containing amino acids at positions 78 through 92 in orf125. A unique band of approximately 17 kDa was detected in the cms-rapeseed sample, which is not found in either fertile rapeseed carrying normal mitochondria or in a fertile revertant line of rapeseed (FIG. 9A). Next, mitochondrial proteins isolated from the cms-rapeseed were separated into soluble and membrane fractions and subjected to Western analysis using the antibody described above. It was found that the 17 kDa polypeptide was present in the membrane fraction of cms-rapeseed mitochondria (FIG. 9B). Thus, it was presumed that orf125 functions similar to urf13 the product of the maize cms gene, i.e. it is localized in the mitochondrial membrane where it interferes with normal mitochondrial function (Proc. Natl. Acad. Sci. USA, 84, 5374–5378 (1987); Science, 239, 293–295 (1988); Proc. Natl. Acad. Sci. USA, 86, 4435–4439 (1989); EMBO J., 9, 339–347 (1990)).

Figure 10A:
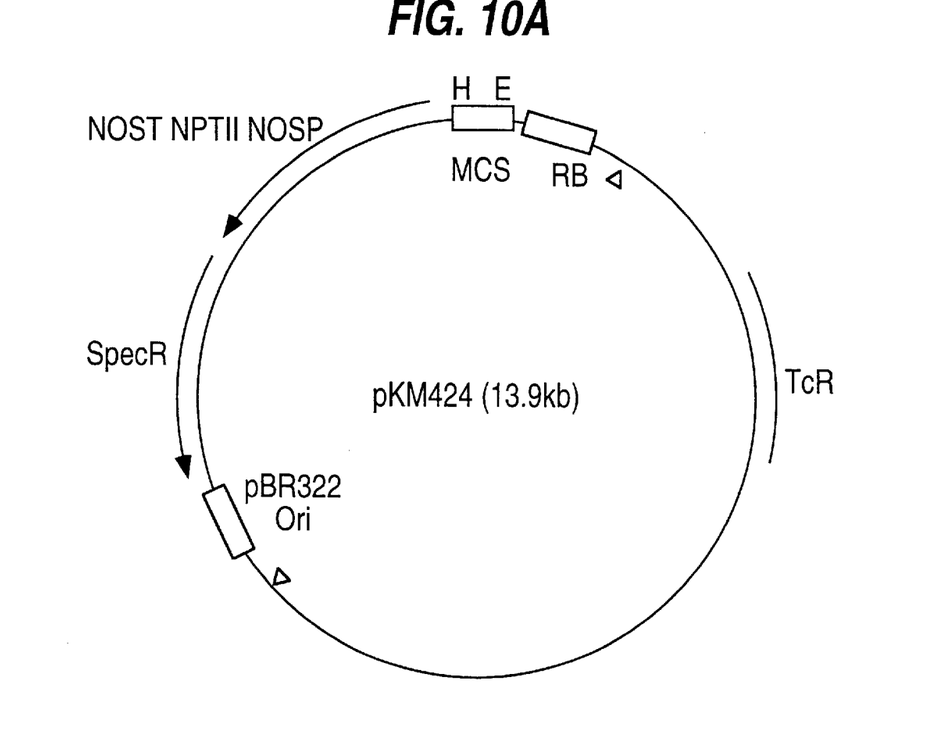
Figure 10B:
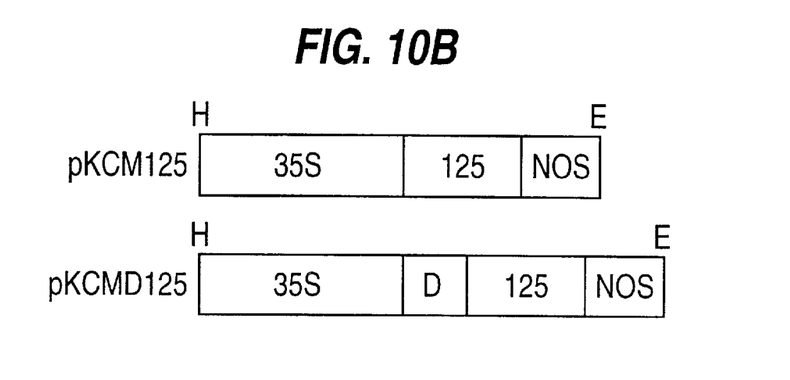

The effect of orf125 on plant cells was examined by introducing the orf125 gene into tobacco plants using the Agrobacterium method. The orf125 gene and a chimeric gene composed of orf125 fused to the sorting sequence to mitochondria, derived from the potato $F_0$–$F_1$ ATPase δ subunit (Plant Cell Phyiols., 34, 177–183 (1993) were linked to the Cauliflower Mosaic Virus 35S promoter (35S) and the Nopaline synthase gene terminator (NOST) and inserted into the HindIII-EcoRI-digested multicloning site of the binary vector pKM424 to produce pKCM125 and pKCMD125, respectively (FIG. 10A, B). As a control vector, the plasmid pLAN411 containing 35S, the β-glucuronidase gene (GUS) and NOST (Plant Cell Rep., 10, 286–290 (1991)). Each of the above binary vectors was introduced into the Agrobacterium strain EHA101 by the freeze/thaw method. Transformation of tobacco was achieved by the method of Rogers et al. (Methods Enzymol., 118, 627–640 (1986)) as follows. EHA101 transformed with each binary vectors was cultured in YEB medium containing 50 μg/ml Spectinomycin, 2.5 μg/ml Tetracycline, and 50 μg/ml Kanamycin for 16 hrs. shaking at 27° C. Approximate 1 cm square-cut pieces of sterilized tobacco leaf were floated in MS medium containing 3% sucrose (approximately 20 pieces per experiment), and cultures of Agrobacterium prepared as described above were mixed with the MS medium at a 1:50 (Agrobacterium:MS) ratio. These were co-cultured by allowing them to stand for 2 days at 27° C. After the co-culturing, tobacco leaf pieces were placed on MS medium containing 0.2 mg/l 6-benzyl-aminopurin, 200 μg/ml Kanamycin, 500 μg/ml Claforan, 3% sucrose and 0.2% Gelrite and cultured at 27° C. for 20 days. The regeneration frequency of plants cultured in this experiment was calculated as the number of transformed adventitious buds per total number of leaf pieces. These results are shown in Table 5.

TABLE 5

Effect of transformation of orf125 on adventitious bud formation in plants

| Experiment number | Rate of adventitious bud formation per leaf piece | | |
|---|---|---|---|
| | pLAN411 | pKCM125 | pKCMD125 |
| 1 | 0.46 | 0.32 | 0.14 |
| 2 | 0.83 | 0.13 | 0.02 |
| 3 | 0.33 | — | 0.12 |
| 4 | 1.10 | — | — |
| 5 | 0.67 | — | — |

These results show that the rate of adventitious bud formation per leaf piece in samples transformed by pLAN411 averaged 0.68, whereas those transformed by pKCM125 and pKCMD125 averaged 0.22 and 0.07, respectively. In addition, it was found that when tobacco leaf pieces from which adventitious buds had formed were cultured and transferred to fresh MS medium prepared as described above and cultured further, and then adventitious bud was cut off from the leaf piece when the adventitious buds had reached 1–2 cm, and grown on MS medium without Kanamycin and 6-purine, and morphology was investigated. The investigation revealed that the plants into which GUS had been introduced developed with normal morphology whereas plants into which orf125 had been introduced exhibited an unusual vitrified morphology at a high frequency (Table 6).

TABLE 6

Effect of orf125 on morphology of regenerated plants'

| Vector | Number of regenerated individuals | Morphological aberrations | |
|---|---|---|---|
| | | Number | % |
| pLAN411 | 30 | 0 | 0 |
| pKCM125 | 16 | 3 | 19 |
| pKCMD125 | 30 | 13 | 81 |

The above results show that the presence of orf125 in the mitochondria has an effect on morphogenesis of plant cells and suggests that it is possible to produce male-sterile plants by the introduction of orf125 into plants via transformation.

The present invention provides a novel cms cytoplasmic gene which is valuable in the production of hybrid plant seed, for example, of the Cruciferae family. This invention is also useful for rapidly identifying Kosena cms cytoplasm, a novel cytoplasm which exhibits characteristics useful for plant breeding.

In addition, this gene may possibly be used to confer CMS onto a broad range of plant species, not limited to those of the Cruciferae family, by its introduction into the nuclear or mitochondrial genomes.

We claim:

1. An isolated gene encoding a polypeptide having the amino acid sequence of Sequence ID No:1.

2. The isolated gene of claim 1, wherein said gene has the nucleotide sequence of Sequence ID No:1.

3. The isolated gene of claim 2, wherein said gene is derived from Kosena radish.

4. An isolated DNA fragment having the nucleotide sequence of Sequence ID No:4.

5. A transgenic plant into which the gene of claim 1 has been introduced.

6. A transgenic plant into which the DNA fragment of claim 4 has been introduced.

7. The transgenic plant of claim 6, wherein said plant is of the Cruciferae family.

8. The transgenic plant of claim 7, wherein said plant is rapeseed.

9. A transgenic plant into which the gene of claim 2 has been introduced.

10. A method of producing a hybrid plant comprising crossing the transgenic plant of any one of claims 5 or 9 carrying cytoplasmic male sterility as a pollen recipient with a plant, into which a fertility-restoring gene derived from a cruciferous plant capable of restoring a pollen fertility has been introduced, as a pollen donor.

11. A hybrid plant produced by the method of claim 10.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 659 bases
        ( B ) TYPE: nucleic acid
        ( C ) STRANDEDNESS: double
        ( D ) TOPOLOGY: linear     ( i i ) MOLECULE TYPE: genomic DNA     ( v i ) ORIGINAL SOURCE:
        ( A ) ORGANISM: Raphanus sativus
        ( B ) STRAIN: Kosena radish
        ( I ) ORGANELLE: mitochondria     ( x i ) SEQUENCE DESCRIPTION: SEQ ID NO:1:

```
AACTCATCAG  GCTCATGACC  TGAAGATTAC  AGGTTCAAAT  CCTGTCCCCG  CACCGTAGTT                  60

TCATTCTGCA  TCACTCTCCC  TGTCGTTATC  GACCTCGCAA  GGTTTTGAA   ACGGCCGAAA                 120

CGGGAAGTGA  CAATACCGCT  TTTCTTCAGC  ATATAAATGC  A ATG ATT ACC TTT TTC                  176
                                                 Met Ile Thr Phe Phe
                                                  1               5

GAA AAA TTG TCC ACT TTT TGT CAT AAT CTC ACT CCT ACT GAA TGT AAA                        224
Glu Lys Leu Ser Thr Phe Cys His Asn Leu Thr Pro Thr Glu Cys Lys
            10                  15                  20

GTT AGT GTA ATA AGT TTC TTT CTT TTA GCT TTT TTA CTA ATG GCC CAT                        272
Val Ser Val Ile Ser Phe Phe Leu Leu Ala Phe Leu Leu Met Ala His
                25                  30                  35

ATT TGG CTA AGC TGG TTT TCT AAC AAC CAA CAT TGT TTA CGA ACC ATG                        320
Ile Trp Leu Ser Trp Phe Ser Asn Asn Gln His Cys Leu Arg Thr Met
            40                  45                  50

AGA CAT CTA GAG AAG TTA AAA ATT CCA TAT GAA TTT CAG TAT GGG TGG                        368
Arg His Leu Glu Lys Leu Lys Ile Pro Tyr Glu Phe Gln Tyr Gly Trp
```

```
              55                        60                        65
CTA  GGT  GTC  AAA  ATT  ACA  ATA  AAA  TCA  AAT  GTA  CCT  AAC  GAT  GAA  GTG         416
Leu  Gly  Val  Lys  Ile  Thr  Ile  Lys  Ser  Asn  Val  Pro  Asn  Asp  Glu  Val
 70                      75                      80                       85

ACG  AAA  AAA  GTC  TCA  CCT  ATC  ATT  AAA  GGG  GAA  ATA  GAG  GGG  AAA  GAG         464
Thr  Lys  Lys  Val  Ser  Pro  Ile  Ile  Lys  Gly  Glu  Ile  Glu  Gly  Lys  Glu
                90                       95                           100

GAA  AAA  AAA  GAG  GGG  AAA  GGG  GAA  ATA  GAG  GGG  AAA  GAG  GAA  AAA  AAA         512
Glu  Lys  Lys  Glu  Gly  Lys  Gly  Glu  Ile  Glu  Gly  Lys  Glu  Glu  Lys  Lys
               105                           110                      115

GAG  GTG  GAA  AAT  GGA  CCG  AGA  AAA  TAATGCTTTG  TGAACCCAAT  TGCTTTGACA             566
Glu  Val  Glu  Asn  Gly  Pro  Arg  Lys  Stop
          120                      125

AAAATAAAGA  AAGAAGCAAA  ATCTCATTCA  ATTTGAAATA  GAAGAGATCT  CTATGCCCCC                626

TGTTCTTGGT  TTTCTCCCAT  GCTTTTGTTG  GTC                                               659

( 2 ) INFORMATION FOR SEQ ID NO:2:

( i ) SEQUENCE CHARACTERISTICS:
              ( A ) LENGTH: 22 bases
              ( B ) TYPE: nucleic acid
              ( C ) STRANDEDNESS: single
              ( D ) TOPOLOGY: linear ( i i ) MOLECULE TYPE: other nucleic acid, synthetic DNA ( x i ) SEQUENCE DESCRIPTION: SEQ ID NO:2:

GACATCTAGA  GAAGTTAAAA  AT                                                             22

( 2 ) INFORMATION FOR SEQ ID NO:3:

( i ) SEQUENCE CHARACTERISTICS:
              ( A ) LENGTH: 22 bases
              ( B ) TYPE: nucleic acid
              ( C ) STRANDEDNESS: single
              ( D ) TOPOLOGY: linear ( i i ) MOLECULE TYPE: other nucleic acid, synthetic DNA ( x i ) SEQUENCE DESCRIPTION: SEQ ID NO:3:

AGCAATTGAA  TTCACAAAGC  AT                                                             22

( 2 ) INFORMATION FOR SEQ ID NO:4:

( i ) SEQUENCE CHARACTERISTICS:
              ( A ) LENGTH: 1242 bases
              ( B ) TYPE: nucleic acid
              ( C ) STRANDEDNESS: double
              ( D ) TOPOLOGY: linear ( i i ) MOLECULE TYPE: genomic DNA ( v i ) ORIGINAL SOURCE:
              ( A ) ORGANISM: Brassica napus
              ( B ) STRAIN: SW18
              ( I ) ORGANELLE: mitochondria ( x i ) SEQUENCE DESCRIPTION: SEQ ID NO:4:

AACTCATCAG  GCTCATGACC  TGAAGATTAC  AGGTTCAAAT  CCTGTCCCCG  CACCGTAGTT                 60

TCATTCTGCA  TCACTCTCCC  TGTCGTTATC  GACCTCGCAA  GGTTTTGAA   ACGGCCGAAA                120

CGGGAAGTGA  CAATACCGCT  TTTCTTCAGC  ATATAAATGC  AATGATTACC  TTTTCGAAA                 180

AATTGTCCAC  TTTTTGTCAT  AATCTCACTC  CTACTGAATG  TAAAGTTAGT  GTAATAAGTT                240

TCTTTCTTTT  AGCTTTTTTA  CTAATGGCCC  ATATTTGGCT  AAGCTGGTTT  TCTAACAACC                300
```

-continued

| | | | | | | |
|---|---|---|---|---|---|---|
|AACATTGTTT|ACGAACCATG|AGACATCTAG|AGAAGTTAAA|AATTCCATAT|GAATTTCAGT|360|
|ATGGGTGGCT|AGGTGTCAAA|ATTACAATAA|AATCAAATGT|ACCTAACGAT|GAAGTGACGA|420|
|AAAAGTCTC|ACCTATCATT|AAAGGGGAAA|TAGAGGGGAA|AGAGGCAAAA|AAAGAGGGGA|480|
|AAGGGGAAAT|AGAGGGGAAA|GAGGAAAAAA|AAGAGGTGGA|AAATGGACCG|AGAAAATAAT|540|
|GCTTTGTGAA|CCCAATTGCT|TTGACAAAAA|TATATGAAGA|ATCAGTGCTA|TTGAGGAACA|600|
|TTTTATAGAA|AGAAAAGAAA|AAGAAGCAAT|AGTAAAGGAG|GGCTTTCCCA|GTGCATGAAG|660|
|GGAGGGTGAA|GCAGGGTAAG|TCATAAGAAT|CCGCTTTCTT|ACAAAGACCT|CCTGCTATGC|720|
|TAATGAGGGG|TCTTAAGCAA|ACAAAGTACC|AAGAACTTTG|GATATTATCC|GTTTTCTAT|780|
|TATATCCCAT|TTTATCCTTC|CGCTTTAGGA|TTAGCCCAGC|TTTTCGAAA|CGGACGGAAG|840|
|GCCTAACTAG|AAGCTATTTG|GCGCCTTCCC|CTCGATGAAT|ACTTGGAAAT|TTGTCTTGCA|900|
|TCGTAAGCTG|TCAGAAGAAA|GTAAGACTTA|GAAAGAAGAC|AGTAAGTAAG|AGAACTACGA|960|
|TTTACTTGAT|TCCCAAAGTG|GTACGTAGGC|AGCCAAGGAC|GAATCCTTAT|CCAGTTCTTT|1020|
|GTTAGTAAGT|GAGGAAAAGA|TATCAAACTT|TTTTTTGAAA|AAAGTTCGTA|GTTAATCTAC|1080|
|CTCGGACGTA|CCCATGGCGT|GTGGGGTTCG|CGTGGGGAAC|CGAGTAACCA|AAGTCACGAT|1140|
|CAGTCTAAGG|TTGAAATCTG|GATGGTCTTT|TTGCCAGACG|CGCTGGTTCG|AGTCCAGCTC|1200|
|GTGACAAAAG|GCTACCCTTT|CTCTTAAGAG|AATCTCGATA|TC| |1242|

( 2 ) INFORMATION FOR SEQ ID NO:5:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear     ( i i ) MOLECULE TYPE: other nucleic acid, synthetic DNA     ( x i ) SEQUENCE DESCRIPTION: SEQ ID NO:5:

TCTGACAGCT TACGATG        17

( 2 ) INFORMATION FOR SEQ ID NO:6:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear     ( i i ) MOLECULE TYPE: other nucleic acid, synthetic DNA     ( x i ) SEQUENCE DESCRIPTION: SEQ ID NO:6:

CTACCAGAGG TATCTATAGA AT        22